US010105047B2

(12) United States Patent
Li et al.

(10) Patent No.: US 10,105,047 B2
(45) Date of Patent: Oct. 23, 2018

(54) AUTOMATIC UNATTENDED-MONITORING VISUAL ACUITY INSPECTION DEVICE

(71) Applicant: BOE Technology Group Co., Ltd., Beijing (CN)

(72) Inventors: Wenbo Li, Beijing (CN); Yefei Dong, Beijing (CN); Yanbing Wu, Beijing (CN)

(73) Assignee: BOE Technology Group Co., Ltd., Beijing (CN)

( * ) Notice: Subject to any disclaimer, the term of this patent is extended or adjusted under 35 U.S.C. 154(b) by 19 days.

(21) Appl. No.: 15/104,672

(22) PCT Filed: Sep. 22, 2015

(86) PCT No.: PCT/CN2015/090276
§ 371 (c)(1),
(2) Date: Jun. 15, 2016

(87) PCT Pub. No.: WO2016/192250
PCT Pub. Date: Dec. 8, 2016

(65) Prior Publication Data
US 2017/0127934 A1    May 11, 2017

(30) Foreign Application Priority Data
Jun. 5, 2015  (CN) .......................... 2015 1 0303652

(51) Int. Cl.
A61B 3/02         (2006.01)
A61B 3/032        (2006.01)
(Continued)

(52) U.S. Cl.
CPC ............ *A61B 3/032* (2013.01); *A61B 3/0025* (2013.01); *A61B 3/0033* (2013.01); *A61B 3/066* (2013.01);
(Continued)

(58) Field of Classification Search
CPC ..... A61B 3/032; A61B 3/0025; A61B 3/0033; A61B 3/066; G06T 7/70; G02F 1/133528; G06K 9/00362; H04N 7/183
(Continued)

(56) References Cited

U.S. PATENT DOCUMENTS 4,870,486 A    9/1989 Nakagawa et al.
5,026,151 A    6/1991 Walktuck et al.
(Continued)

FOREIGN PATENT DOCUMENTS

CN    1736322 A    2/2006
CN    1775167 A    5/2006
(Continued)

OTHER PUBLICATIONS

Third Office Action, including Search Report, for Chinese Patent Application No. 201510303652.7, dated Nov. 21, 2016, 13 pages.
(Continued)

*Primary Examiner* — James Greece
(74) *Attorney, Agent, or Firm* — Westman, Champlin & Koehler, P.A.

(57) ABSTRACT

An automatic unattended-monitoring visual acuity inspection device is disclosed. The inspection device includes an inspection panel, an inspector and an isolation wall arranged opposite to the inspection panel. The isolation wall is provided with a wireless signal transmitter configured to transmit a visual acuity indication signal to the wireless signal receiver through a network. The wireless signal receiver is configured to transmit the received visual acuity indication signal to a processor. The processor is configured to process the visual acuity indication signal and transmit a process feedback to the inspection panel. The device may prevent achieving a high level of visual acuity of the person to be inspected by cheating behaviors, thereby highly
(Continued)

inspecting a real visual acuity level of the person to be inspected.

20 Claims, 3 Drawing Sheets

(51) Int. Cl.
  G06T 7/70  (2017.01)
  A61B 3/00  (2006.01)
  A61B 3/06  (2006.01)
  G02F 1/1335  (2006.01)
  G06K 9/00  (2006.01)
  H04N 7/18  (2006.01)
(52) U.S. Cl.
  CPC ... *G02F 1/133528* (2013.01); *G06K 9/00362* (2013.01); *G06T 7/70* (2017.01); *H04N 7/183* (2013.01)
(58) Field of Classification Search
  USPC .................................. 351/223, 205–206, 246
  See application file for complete search history.

(56) References Cited

U.S. PATENT DOCUMENTS

| | | | |
|---|---|---|---|
| 5,331,358 A * | 7/1994 | Schurle | A61B 3/032 348/58 |
| 5,444,504 A | 8/1995 | Kobayashi et al. | |
| 5,864,384 A * | 1/1999 | McClure | A61B 3/024 351/224 |
| 7,549,750 B2 | 6/2009 | Nakamura et al. | |
| 7,607,778 B2 | 10/2009 | Oda | |
| 7,690,790 B2 | 4/2010 | Hosoi et al. | |
| 7,883,211 B2 | 2/2011 | Hosoi et al. | |
| 8,167,429 B1 * | 5/2012 | Butler | A61B 5/0002 351/205 |
| 2010/0283969 A1 * | 11/2010 | Cooperstock | A61B 3/022 351/201 |
| 2015/0379911 A1 | 12/2015 | Chen et al. | |

FOREIGN PATENT DOCUMENTS

| | | |
|---|---|---|
| CN | 1883376 A | 12/2006 |
| CN | 1883377 A | 12/2006 |
| CN | 101361648 A | 2/2009 |
| CN | 101426417 A | 5/2009 |
| CN | 101431935 A | 5/2009 |
| CN | 202161299 U | 3/2012 |
| CN | 102920427 A | 2/2013 |
| CN | 203011511 U | 6/2013 |
| CN | 103598872 A | 2/2014 |
| CN | 203828896 U | 9/2014 |
| CN | 104134282 A | 11/2014 |
| CN | 104840180 A | 8/2015 |
| EP | 0 233 636 A2 | 8/1987 |
| EP | 2 014 222 A1 | 1/2009 |
| JP | 8-80280 A | 3/1996 |

OTHER PUBLICATIONS

International Search Report and Written Opinion for International Application No. PCT/CN2015/090276, dated Jan. 18, 2016, 11 pages.
English translation of Box No. V of the Written Opinion from the International Searching Authority for International Application No. PCT/CN2015/090276, dated Jan. 18, 2016, 2 pages.
First Office Action, including Search Report, for Chinese Patent Application No. 201510303652.7, dated Dec. 31, 2015, 10 pages.
Second Office Action, including Search Report, for Chinese Patent Application No. 201510303652.7, dated Jun. 12, 2016, 17 pages.
Extended European Search Report for European Patent Application No. 15868657.6-1666 / 3127471, dated Jul. 19, 2017, 7 pages.

* cited by examiner

AUTOMATIC UNATTENDED-MONITORING VISUAL ACUITY INSPECTION DEVICE

CROSS-REFERENCE TO RELATED APPLICATION

This application is a Section 371 National Stage Application of International Application No. PCT/CN2015/090276, filed on Sep. 22, 2015, entitled "Automatic Unattended-Monitoring Visual Acuity Inspection Device", which claims priority to Chinese Application No. 201510303652.7, filed on Jun. 5, 2015, incorporated herein by reference in their entirety.

BACKGROUND OF THE INVENTION

Field of the Invention

Embodiments of the present disclosure relate to a display technique field for a visual acuity inspection, and more particularly, to an automatic unattended-monitoring visual acuity inspection device.

Description of the Related Art

It is important for eyes to provide a visual perception function, and visual acuity is an important index for evaluating visual function. Visual acuity inspection is a most primary, simple, and rapid method to know the visual function of the eyes. It is not only a primary index to objectively evaluate state of an illness, but also an important basis to aid in eye disease diagnosis and differential diagnosis. It is necessary for routine physical checkup to implement a visual acuity, color blindness inspection, and so on. Furthermore, it puts forward a strict requirement for eye health condition in some specific industry fields or operating posts, for example, aviator, taxi driver, doctor, etc.

In conventional inspections, for example, using a normal visual acuity chart, it is possible to incur many cheating behaviors, such as a reminder from those around a person to be inspected, bearing in mind image information directions and positions on the visual acuity chart, and the like. In addition, there may be cheating behaviors in an automatic inspection without surgeon assistance. All these result in that there is a large distance between inspection result and actual situation, thereby it cannot meet actual inspection requirements.

SUMMARY OF THE INVENTION

I. Technical Problem to be Solved

The technical problem to be solved of the present disclosure is to provide an automatic unattended-monitoring visual acuity inspection device, so as to overcome drawbacks of cheating behavior existing and therefore inaccuracy inspection result and low efficient inspection during conventional visual acuity inspections.

II. Technical Solution

To solve the above technical problem, the present disclosure provides an automatic unattended-monitoring visual acuity inspection device, comprising an inspection panel, an inspector and an isolation wall arranged opposite to the inspection panel;

wherein the inspection panel comprises a liquid crystal display panel, a lower polarizer and a backlight source successively arranged in a direction from human eyes to the inspection panel; the liquid crystal display panel is configured to display visual display pictures; and the inspection panel further comprises a wireless signal receiver and a processor;

wherein the isolation wall is provided with a wireless signal transmitter configured to transmit a visual acuity indication signal collected from a person to be inspected to the wireless signal receiver through a network;

wherein the wireless signal receiver is configured to transmit the received visual acuity indication signal to the processor, and the processor is configured to process the visual acuity indication signal and transmit a process feedback to the inspection panel;

wherein the inspector comprises a liquid crystal cell, and an outer polarizer and an inner polarizer are provided on an upper surface and a lower surface of the liquid crystal cell, respectively, and a light-transmitting direction of a transmitting axis of the outer polarizer is identical to a light-transmitting direction of a transmitting axis of the lower polarizer of the inspection panel.

Optionally, processing the visual acuity indication signal and transmitting the process feedback to the inspection panel by the processor comprise:

comparing the currently received visual acuity indication signal with a pre-stored standard visual acuity inspection signal, and feeding back a comparison result to the inspection panel, and determining whether all the visual display pictures have been applied to inspection, if not, then providing next visual display picture to implement the inspection, if yes, then prompting that inspection operation has been completed, and storing and outputting an inspection result.

Optionally, the isolation wall is provided with a touch direction rod, and the visual acuity indication signal of the person to be inspected is transmitted to the wireless signal transmitter by operating the touch direction rod.

Optionally, the isolation wall is provided with a sound sensor, and the visual acuity indication signal of the person to be inspected is transmitted to the wireless signal transmitter by collecting a sound signal of the person to be inspected.

Optionally, the inspector is integrated on the isolation wall and connected with a lifting rod, and the inspector is driven to perform a lifting motion by the lifting rod under an action of a lifting controller.

Optionally, at least one image capturing module is provided at a top of the isolation wall to detect a stature of the person to be inspected, and a calculation formula of the stature of the person to be inspected is as follows:

$$h_2 = h_1 - (L^2 - d_1^2)^{1/2}$$

where $h_2$ is the stature of the person to be inspected, $d_1$ is a distance between the person to be inspected and the isolation wall, $h_1$ is a height of the image capturing module on the isolation wall, and L is a distance between the image capturing module and a head of the person to be inspected, which is acquired by the image capturing module.

Optionally, a weight sensor is provided on a bottom of the isolation wall to detect a weight of the person to be inspected.

Optionally, the calculation formula of the stature $h_2$ of the person to be inspected is as follows:

$$h_2 = h_1 - (L^2 - d_1^2)^{1/2} - h_3$$

wherein $h_3$ is an inherent height of the weight sensor.

Optionally, the inspector is a pair of shutter glasses provided with a master control power switch and two selectively reversing switches configured to switch a closed or open state of two spectacle lenses, respectively.

Optionally, the visual display pictures comprise a standard visual acuity inspection chart or a color-blindness inspection picture.

III. Advantageous Effect

In the present disclosure, there is provided an automatic unattended-monitoring visual acuity inspection device. By means of the cooperated liquid crystal cell and lower polarizer in the inspector, the person to be inspected may effectively see display contents in the visual display pictures only if he or she wears the inspector. Therefore, the device may prevent achieving a high level of visual acuity of the person to be inspected by cheating behaviors, such as remembering position information regarding an inspection chart or reminding the person to be inspected by other persons. In addition, it may automatically implement visual acuity inspection operation in an unattended-monitoring condition, thereby highly improving inspection efficiency and reliably inspecting a real visual acuity level of the person to be inspected. The device is suitable for applying in those occasions where a strict requirement for visual acuity inspection is needed.

DETAILED DESCRIPTION OF PREFERRED EMBODIMENTS OF THE INVENTION

The implementation of the present disclosure will be further described in detail below, in combination with the accompanying figures and the embodiments. The embodiments hereafter is intended to describe the present disclosure, rather than limiting protection scope of the present disclosure.

Figure 1:
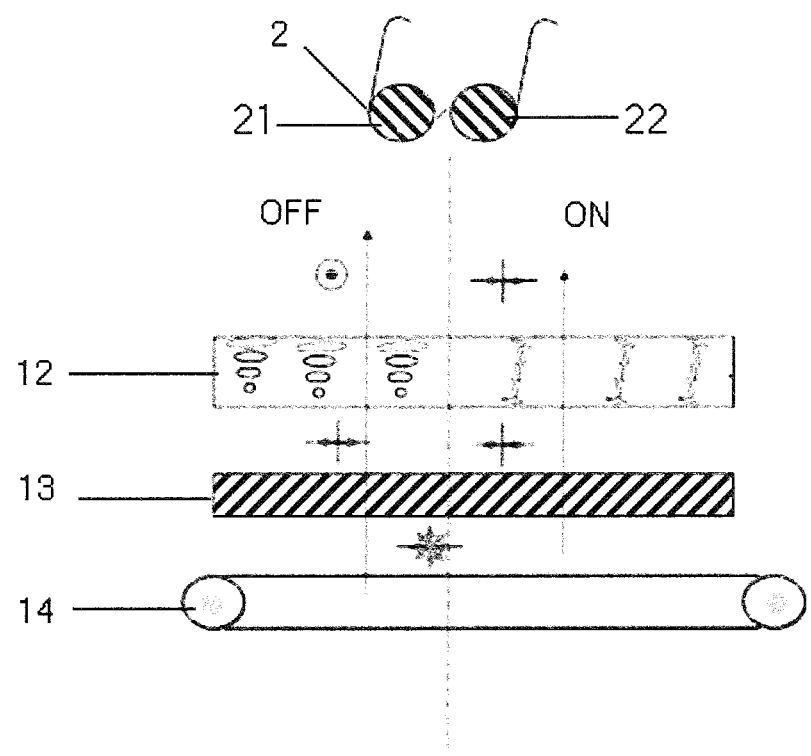
FIG. 1 is a schematic view of an automatic unattended-monitoring visual acuity inspection device according to an embodiment of the present disclosure, with an inspector.
Figure 2:
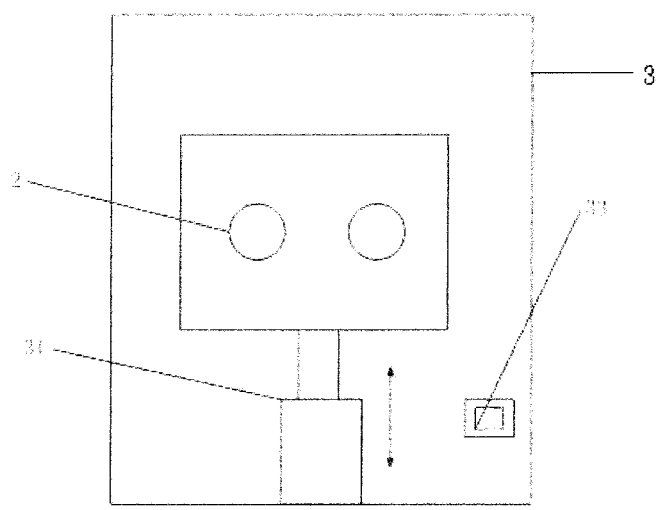
FIG. 2 is a schematic view of an isolation wall in the automatic unattended-monitoring visual acuity inspection device according to an embodiment of the present disclosure.

As shown in FIGS. 1-2, the present disclosure provides an automatic unattended-monitoring visual acuity inspection device, comprising an inspection panel, an inspector 2 and an isolation wall 3 arranged opposite to the inspection panel.

The inspection panel comprises a liquid crystal display panel 12, a lower polarizer 13 and a backlight source 14 successively arranged in a direction from human eyes to the inspection panel; the liquid crystal display panel 12 is configured to display visual display pictures; and the inspection panel further comprises a wireless signal receiver and a processor.

The isolation wall 3 is provided with a wireless signal transmitter configured to transmit a visual acuity indication signal collected from a person to be inspected to the wireless signal receiver through a network.

The wireless signal receiver is configured to transmit the received visual acuity indication signal to the processor, and the processor is configured to process the visual acuity indication signal and transmit a process feedback to the inspection panel.

The inspector 2 comprises a liquid crystal cell, and an outer polarizer 21 and an inner polarizer 22 are provided on an upper surface and a lower surface of the liquid crystal cell, respectively, and a light-transmitting direction of a transmitting axis of the outer polarizer 21 is identical to a light-transmitting direction of a transmitting axis of the lower polarizer 13 of the inspection panel.

Specifically, the step of processing the visual acuity indication signal and transmitting the process feedback to the inspection panel by the processor comprises:

comparing the currently received visual acuity indication signal with a pre-stored standard visual acuity inspection signal, feeding back a comparison result to the inspection panel, and determining whether all the visual display pictures have been applied to inspection, if not, then providing next visual display picture to implement the inspection, if yes, then prompting that inspection operation has been completed, and storing and outputting an inspection result.

Further, the isolation wall 3 is provided with a touch direction rod 33, and the visual acuity indication signal of the person to be inspected is transmitted to the wireless signal transmitter by operating the touch direction rod 33.

Optionally, the isolation wall is provided with a sound sensor, and the visual acuity indication signal of the person to be inspected is transmitted to the wireless signal transmitter by collecting a sound signal of the person to be inspected.

Optionally, the inspector 2 is integrated on the isolation wall 3 and connected with a lifting rod 31, and the inspector 2 is driven to perform a lifting motion by the lifting rod 31 under an action of a lifting controller.

Figure 3:
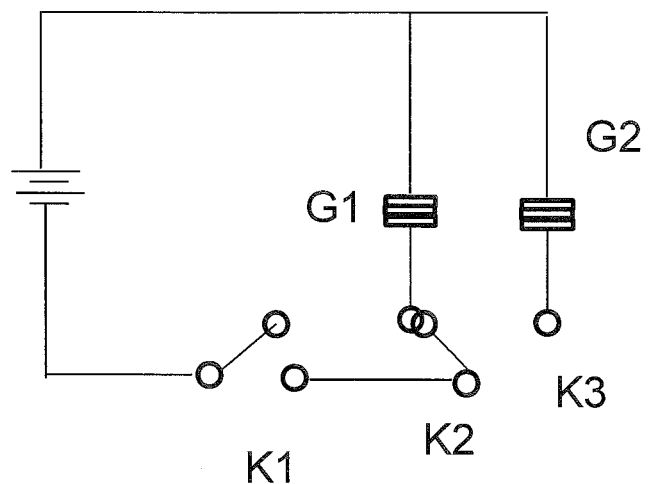
FIG. 3 is a circuit control principle diagram of a pair of shutter glasses in the automatic unattended-monitoring visual acuity inspection device according to an embodiment of the present disclosure.

Optionally, the inspector 2 is a pair of shutter glasses provided with a master control power switch K1 and two selectively reversing switches K2 and K3, wherein K2 is used to control a spectacle lens G1, and K3 is used to control a spectacle lens G2. As for K2, K3, at the same time, one is in closed condition, while the other is in open condition, wherein a control circuit thereof is shown in FIG. 3.

Figure 4:
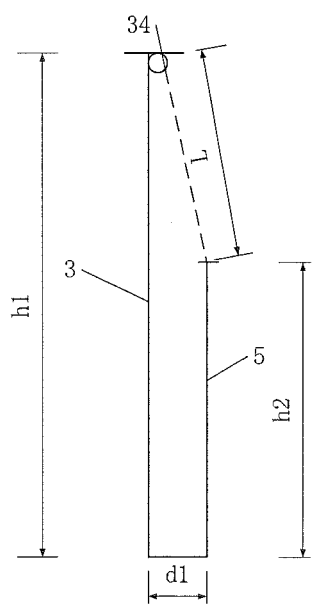
FIG. 4 is a schematic structure view showing a stature calculation method for the automatic unattended-monitoring visual acuity inspection device according to an embodiment of the present disclosure.

In addition, a stature of the person to be inspected may be measured while inspecting the visual acuity thereof. As shown in FIG. 4, at least one image capturing module 34 is provided at a top of the isolation wall to detect the stature of the person to be inspected, and a calculation formula of the stature of the person to be inspected is as follows:

$$h_2 = h_1 - (L^2 - d_1^2)^{1/2}$$

where $h_2$ is the stature of the person to be inspected, $d_1$ is a distance between the person to be inspected and the isolation wall, $h_1$ is a height of the image capturing module (for example, a camera) on the isolation wall, and L is a distance between the image capturing module 34 and a head of the person to be inspected, which is acquired by the image capturing module 34.

In addition, a weight of the person to be inspected may be measured while inspecting the stature thereof. A weight sensor is provided on a bottom of the isolation wall to detect the weight of the person to be inspected.

Figure 5:
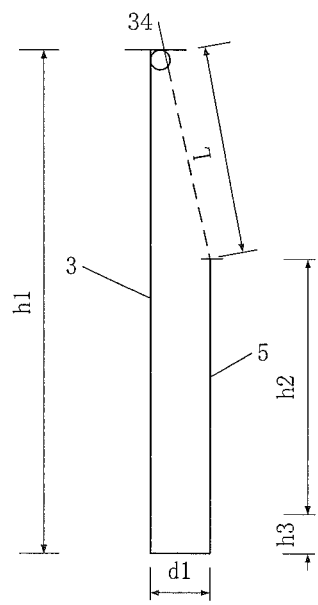
FIG. 5 is a schematic structure view showing a stature calculation method by measuring weight for the automatic unattended-monitoring visual acuity inspection device according to an embodiment of the present disclosure.

As shown in FIG. 5, the calculation formula of the stature $h_2$ of the person to be inspected is as follows:

$$h_2 = h_1 - (L^2 - d_1^2)^{1/2} - h_3$$

wherein $h_3$ is an inherent height of the weight sensor.

In the present embodiment, the visual display picture is a standard visual acuity inspection chart (i.e., a visual acuity E inspection chart) or a color-blindness inspection picture, that is, the visual acuity inspection device in the present embodiment may inspect not only the visual acuity, but also the color-blindness level.

Figure 6:
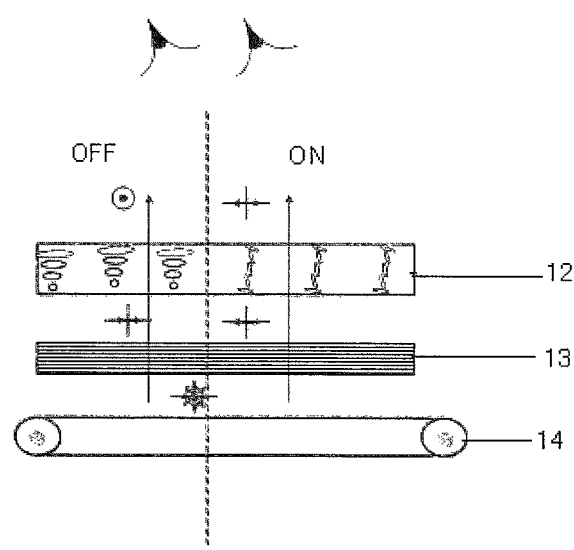
FIG. 6 is a schematic view of the automatic unattended-monitoring visual acuity inspection device according to an embodiment of the present disclosure, in a naked eye condition.

Referring to FIG. 6, a schematic view of the visual acuity inspection device without the inspector, i.e., in a naked eye condition, after the visual acuity inspection device is switched on, an optical axis of the lower polarizer 13 does not change when the inspector 2 is not available. At this time, the light ray will be emitted out as white light, no matter what condition the liquid crystal molecules are in, and a blank screen will be seen when the person to be inspected views the visual display picture, i.e., no contents in the visual display picture will be seen, therefore, the other persons (i.e., with naked eye) cannot provide any hint or direction.

Referring to FIG. 1, a schematic view of the visual acuity inspection device with the inspector, after the visual acuity inspection device is switched on, the liquid crystal molecules will be deflected. At this time, the contents in the visual display picture may be emitted out after the person to be inspected wears the inspector 2, thus, only the person to be inspected wearing the inspector can see the contents in the visual display picture.

In the state that the person to be inspected wears the inspector, he or she follows instructions of an instructor to independently determine an up, down, left or right direction of "E", thereby reducing inputs from an external information source.

In order to prevent the person to be inspected remembering position information, the real direction of the pattern "E" in each line may be changed randomly, so as to prevent performing a cheating determination by remembering the position information.

In addition, it is possible to timely adjust a viewing distance according to display brightness of the image or scaling of the image, so as to satisfy actual viewing requirement. For example, the inspection may be performed with a viewing distance of 5 m in a normal display brightness, and performed with a viewing distance of 2.5 m when the brightness is reduced by a half.

In addition, the inspection panel is provided on a support, and may be stably supported in a position to be placed, to facilitate operating.

In the present disclosure, there is provided an automatic unattended-monitoring visual acuity inspection device. By means of the cooperated liquid crystal cell and lower polarizer in the inspector, the person to be inspected may effectively see display contents in the visual display pictures only if he or she wears the inspector. Therefore, the device may prevent achieving a high level of visual acuity of the person to be inspected by cheating behaviors, such as remembering position information regarding an inspection chart or reminding the person to be inspected by other persons. In addition, it may automatically implement visual acuity inspection operation in an unattended-monitoring condition, thereby highly improving inspection efficiency and reliably inspecting a real visual acuity level of the person to be inspected. The device is suitable for applying in those occasions where a strict requirement for visual acuity inspection is needed.

The above embodiments are merely preferable embodiments of the present disclosure, it should be noted that several changes and substitutions may be made to the present disclosure by the person skilled in the art without departing from the spirit and scope of the present disclosure, and these changes and substitutions fall into the scope of the present disclosure.

What is claimed is:

1. An automatic unattended-monitoring visual acuity inspection device, comprising an inspection panel, an inspector and an isolation wall arranged opposite to the inspection panel;

wherein the inspection panel comprises a liquid crystal display panel, a lower polarizer and a backlight source successively arranged in a direction from human eyes to the inspection panel; the liquid crystal display panel is configured to display visual display pictures; and the inspection panel further comprises a wireless signal receiver and a processor;

wherein the isolation wall is provided with a wireless signal transmitter configured to transmit a visual acuity indication signal collected from a person to be inspected to the wireless signal receiver through a network;

wherein the wireless signal receiver is configured to transmit the received visual acuity indication signal to the processor, and the processor is configured to process the visual acuity indication signal and transmit a process feedback to the inspection panel;

wherein the inspector comprises a liquid crystal cell, and an outer polarizer and an inner polarizer are provided on an upper surface and a lower surface of the liquid crystal cell, respectively, and a light-transmitting direction of a transmitting axis of the outer polarizer is identical to a light-transmitting direction of a transmitting axis of the lower polarizer of the inspection panel.

2. The automatic unattended-monitoring visual acuity inspection device according to claim 1, wherein processing the visual acuity indication signal and transmitting the process feedback to the inspection panel by the processor comprise:

comparing the currently received visual acuity indication signal with a pre-stored standard visual acuity inspection signal, and feeding back a comparison result to the inspection panel, and determining whether all the visual display pictures have been applied to inspection, if not, then providing next visual display picture to implement the inspection, if yes, then prompting that inspection operation has been completed, and storing and outputting an inspection result.

3. The automatic unattended-monitoring visual acuity inspection device according to claim 1, wherein the isolation wall is provided with a touch direction rod, and the visual acuity indication signal of the person to be inspected is transmitted to the wireless signal transmitter by operating the touch direction rod.

4. The automatic unattended-monitoring visual acuity inspection device according to claim 1, wherein the isolation wall is provided with a sound sensor, and the visual acuity indication signal of the person to be inspected is transmitted to the wireless signal transmitter by collecting a sound signal of the person to be inspected.

5. The automatic unattended-monitoring visual acuity inspection device according to claim 1, wherein the inspector is integrated on the isolation wall and connected with a lifting rod, and the inspector is driven to perform a lifting motion by the lifting rod under an action of a lifting controller.

6. The automatic unattended-monitoring visual acuity inspection device according to claim 1, wherein at least one image capturing module is provided at a top of the isolation wall to detect a stature of the person to be inspected, and a calculation formula of the stature of the person to be inspected is as follows:

$$h_2 = h_1 - (L^2 - d_1^2)^{1/2}$$

where $h_2$ is the stature of the person to be inspected, $d_1$ is a distance between the person to be inspected and the isolation wall, $h_1$ is a height of the image capturing module on the isolation wall, and L is a distance between the image capturing module and a head of the person to be inspected, which is acquired by the image capturing module.

7. The automatic unattended-monitoring visual acuity inspection device according to claim 6, wherein a weight sensor is provided on a bottom of the isolation wall to detect a weight of the person to be inspected.

8. The automatic unattended-monitoring visual acuity inspection device according to claim 7, wherein the calculation formula of the stature $h_2$ of the person to be inspected is as follows:

$$h_2 = h_1 - (L^2 - d_1^2)^{1/2} - h_3$$

wherein $h_3$ is an inherent height of the weight sensor.

9. The automatic unattended-monitoring visual acuity inspection device according to claim 1, wherein the inspector is a pair of shutter glasses provided with a master control power switch and two selectively reversing switches configured to switch a closed or open state of two spectacle lenses, respectively.

10. The automatic unattended-monitoring visual acuity inspection device according to claim 1, wherein the visual display pictures comprise a standard visual acuity inspection chart or a color-blindness inspection picture.

11. The automatic unattended-monitoring visual acuity inspection device according to claim 2, wherein the isolation wall is provided with a touch direction rod, and the visual acuity indication signal of the person to be inspected is transmitted to the wireless signal transmitter by operating the touch direction rod.

12. The automatic unattended-monitoring visual acuity inspection device according to claim 2, wherein the isolation wall is provided with a sound sensor, and the visual acuity indication signal of the person to be inspected is transmitted to the wireless signal transmitter by collecting a sound signal of the person to be inspected.

13. The automatic unattended-monitoring visual acuity inspection device according to claim 2, wherein the inspector is integrated on the isolation wall and connected with a lifting rod, and the inspector is driven to perform a lifting motion by the lifting rod under an action of a lifting controller.

14. The automatic unattended-monitoring visual acuity inspection device according to claim 3, wherein the inspector is integrated on the isolation wall and connected with a lifting rod, and the inspector is driven to perform a lifting motion by the lifting rod under an action of a lifting controller.

15. The automatic unattended-monitoring visual acuity inspection device according to claim 4, wherein the inspector is integrated on the isolation wall and connected with a lifting rod, and the inspector is driven to perform a lifting motion by the lifting rod under an action of a lifting controller.

16. The automatic unattended-monitoring visual acuity inspection device according to claim 11, wherein the inspector is integrated on the isolation wall and connected with a lifting rod, and the inspector is driven to perform a lifting motion by the lifting rod under an action of a lifting controller.

17. The automatic unattended-monitoring visual acuity inspection device according to claim 12, wherein the inspector is integrated on the isolation wall and connected with a lifting rod, and the inspector is driven to perform a lifting motion by the lifting rod under an action of a lifting controller.

18. The automatic unattended-monitoring visual acuity inspection device according to claim 2, wherein at least one image capturing module is provided at a top of the isolation wall to detect a stature of the person to be inspected, and a calculation formula of the stature of the person to be inspected is as follows:

$$h_2 = h_1 - (L^2 - d_1^2)^{1/2}$$

where $h_2$ is the stature of the person to be inspected, $d_1$ is a distance between the person to be inspected and the isolation wall, $h_1$ is a height of the image capturing module on the isolation wall, and L is a distance between the image capturing module and a head of the person to be inspected, which is acquired by the image capturing module.

19. The automatic unattended-monitoring visual acuity inspection device according to claim 3, wherein at least one image capturing module is provided at a top of the isolation wall to detect a stature of the person to be inspected, and a calculation formula of the stature of the person to be inspected is as follows:

$$h_2 = h_1 - (L^2 - d_1^2)^{1/2}$$

where $h_2$ is the stature of the person to be inspected, $d_1$ is a distance between the person to be inspected and the isolation wall, $h_1$ is a height of the image capturing module on the isolation wall, and L is a distance between the image capturing module and a head of the person to be inspected, which is acquired by the image capturing module.

20. The automatic unattended-monitoring visual acuity inspection device according to claim 4, wherein at least one image capturing module is provided at a top of the isolation wall to detect a stature of the person to be inspected, and a calculation formula of the stature of the person to be inspected is as follows:

$$h_2 = h_1 - (L^2 - d_1^2)^{1/2}$$

where $h_2$ is the stature of the person to be inspected, $d_1$ is a distance between the person to be inspected and the isolation wall, $h_1$ is a height of the image capturing module on the isolation wall, and L is a distance between the image capturing module and a head of the person to be inspected, which is acquired by the image capturing module.

* * * * *